(12) United States Patent
Ruebben

(10) Patent No.: US 12,263,319 B2
(45) Date of Patent: Apr. 1, 2025

(54) REDUCTION IN DIAMETER

(71) Applicant: Alexander Ruebben, Monaco (MC)

(72) Inventor: Alexander Ruebben, Monaco (MC)

( * ) Notice: Subject to any disclaimer, the term of this patent is extended or adjusted under 35 U.S.C. 154(b) by 393 days.

(21) Appl. No.: 17/641,450

(22) PCT Filed: Aug. 12, 2020

(86) PCT No.: PCT/EP2020/072571
§ 371 (c)(1),
(2) Date: Mar. 9, 2022

(87) PCT Pub. No.: WO2021/047848
PCT Pub. Date: Mar. 18, 2021

(65) Prior Publication Data
US 2022/0387769 A1 Dec. 8, 2022

(30) Foreign Application Priority Data

Sep. 9, 2019 (DE) .................. 10 2019 124 056.5
Apr. 30, 2020 (DE) .................. 10 2020 111 805.8

(51) Int. Cl.
*A61M 25/10* (2013.01)

(52) U.S. Cl.
CPC . *A61M 25/1038* (2013.01); *A61M 2025/1004* (2013.01); *A61M 2025/1081* (2013.01)

(58) Field of Classification Search
CPC .. A61M 2025/1081; A61M 2025/1004; A61M 25/1029; A61M 25/1038; A61M 25/1002; A61M 25/10; A61M 25/104; A61M 2025/1088; A61F 2/958; A61F 2/95; B29C 63/0056; B29C 63/18; B29L 2031/7542
See application file for complete search history.

(56) References Cited

U.S. PATENT DOCUMENTS

2016/0166810 A1* 6/2016 Pigott .................. A61M 25/10
604/103.05
2017/0291015 A1* 10/2017 Ruebben ........... A61M 25/1038

FOREIGN PATENT DOCUMENTS

| JP | 2003-062081 | 3/2003 | |
| JP | 2005-211492 | 8/2005 | |
| WO | WO 2013/066566 | 5/2013 | |
| WO | WO-2014076776 A1 * | 5/2014 | ........ A61M 25/1038 |
| WO | WO 2016/050303 | 4/2016 | |

OTHER PUBLICATIONS

Internationaler Recherchenbericht und Schriftlicher Bescheid [International Search Report and the Written Opinion] Dated Dec. 10, 2020 From the International Searching Authority Re. Application No. PCT/EP2020/072571 and its Translation of Search Report Into English. (13 Pages).

* cited by examiner

*Primary Examiner* — Katherine M Shi

(57) ABSTRACT

The invention relates to a method for reducing the outer diameter of the balloon (1) of a balloon catheter in the non-expanded state, wherein at least one restriction element (3) is applied to at least a portion of the balloon (1) of the balloon catheter. In this way, the outer diameter of the balloon (1) is thus reduced and, moreover, its flexibility increased.

13 Claims, 2 Drawing Sheets

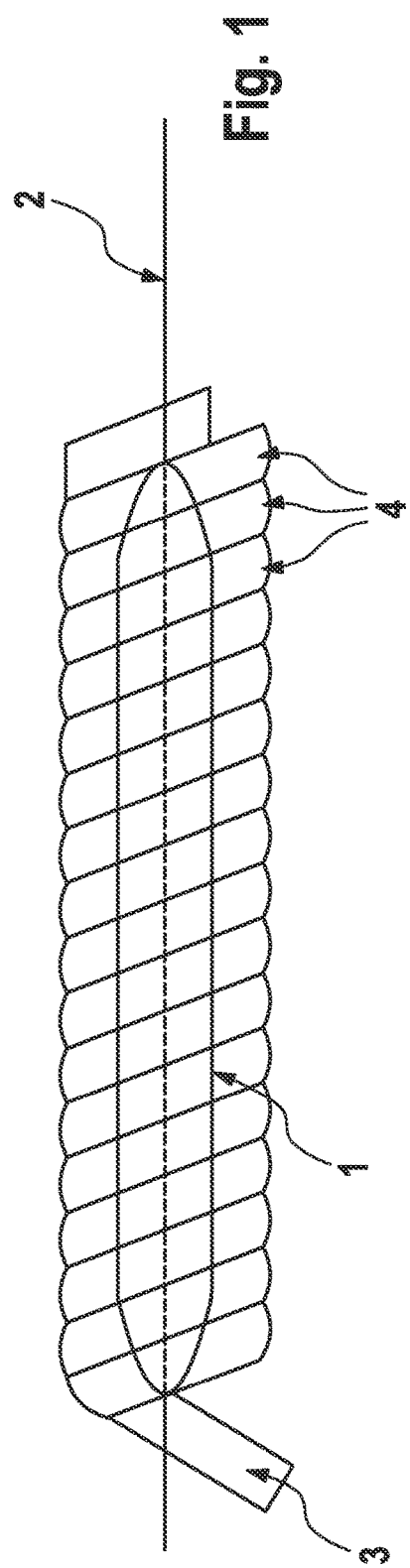
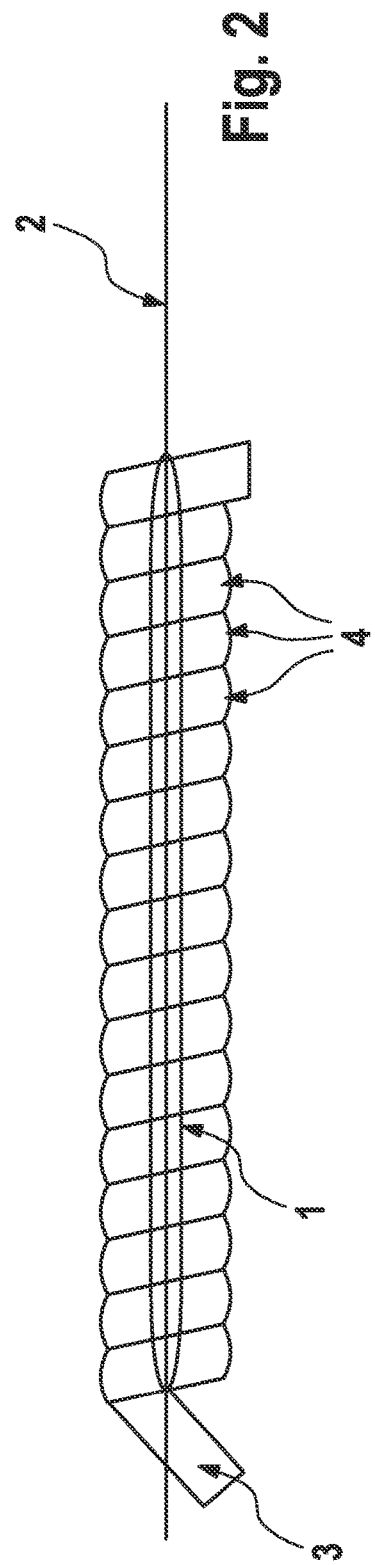
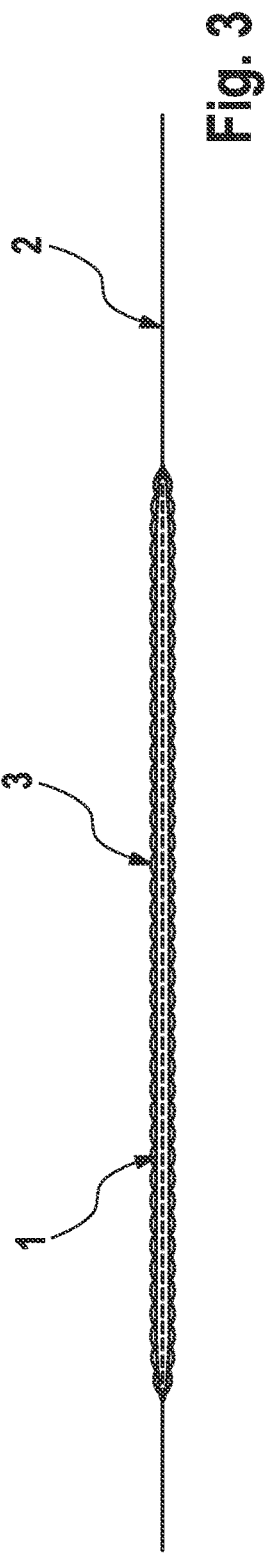

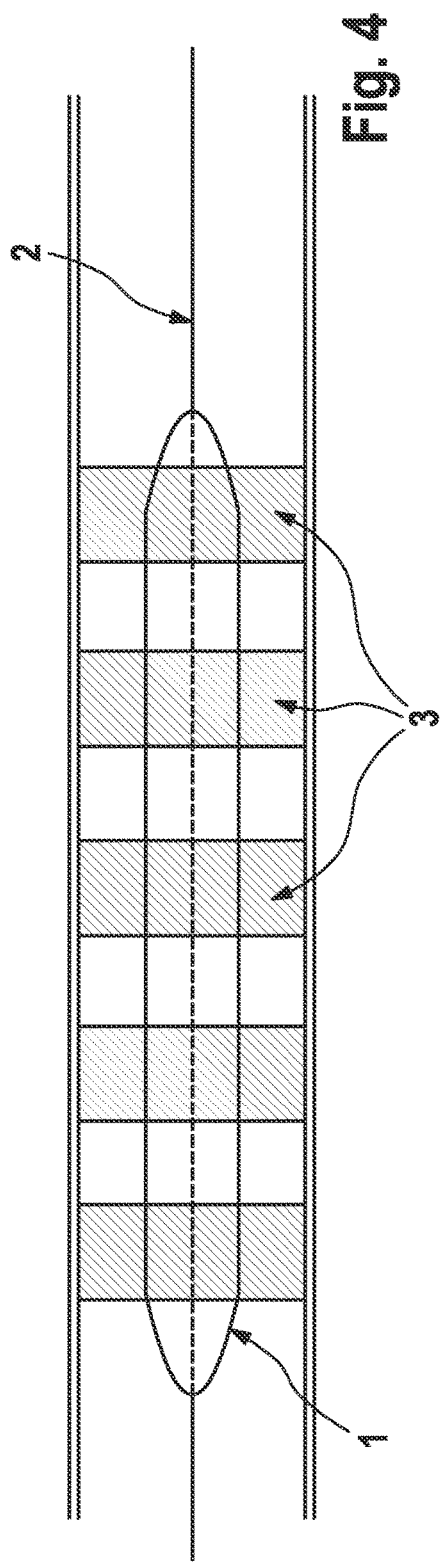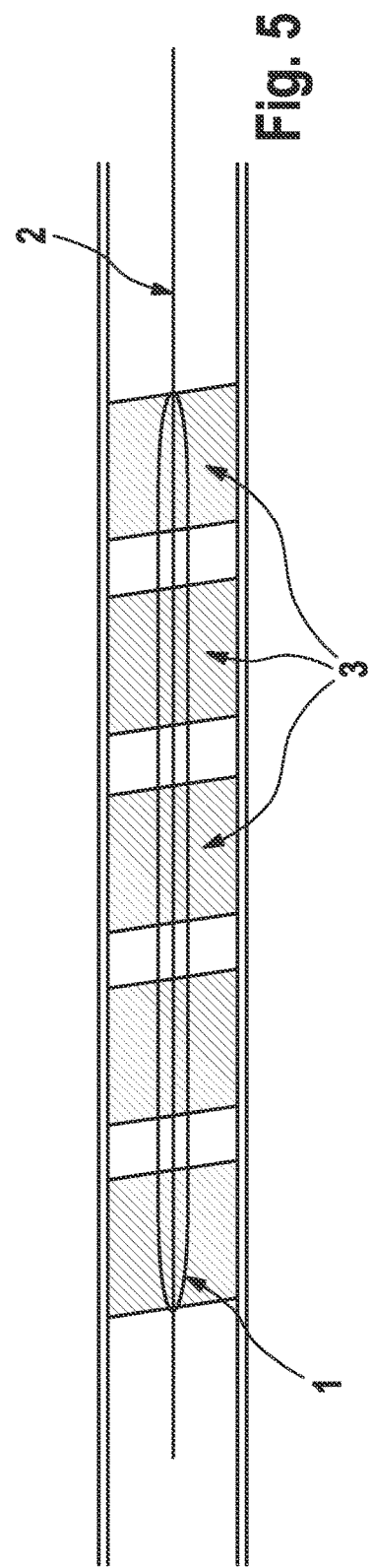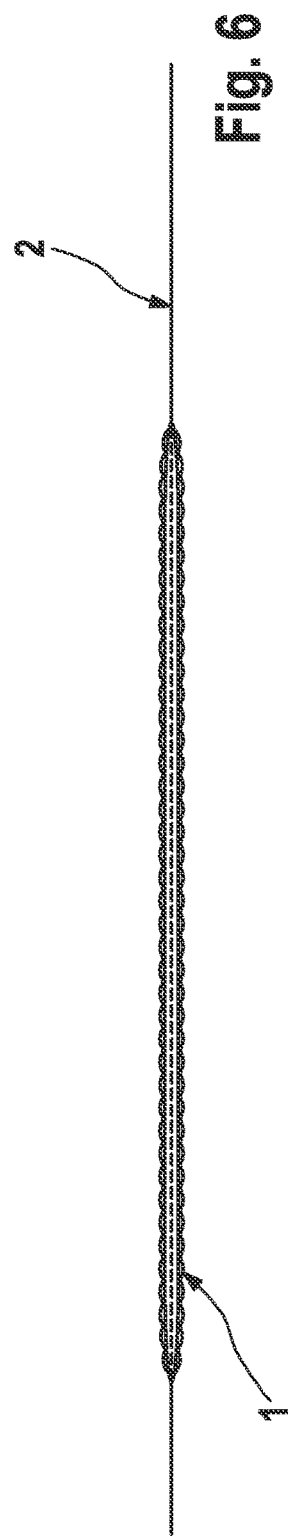

REDUCTION IN DIAMETER

RELATED APPLICATIONS

This application is a National Phase of PCT Patent Application No. PCT/EP2020/072571 having International filing date of Aug. 12, 2020, which claims the benefit of priority of Germany Patent Application Nos. 10 2020 111 805.8 filed on Apr. 30, 2020 and 10 2019 124 056.5 filed on Sep. 9, 2019. The contents of the above applications are all incorporated by reference as if fully set forth herein in their entirety.

FIELD AND BACKGROUND OF THE INVENTION

The invention relates to a method aimed at reducing the outer diameter of the balloon of a balloon catheter in the deflated state.

Nowadays, the application of balloon catheters is a standard procedure in everyday clinical practice. Their use in the context of intravascular interventions usually involves the widening of constricted vessel locations, either by means of the balloon catheter itself or in combination with other medical devices such as balloon-expandable stents.

Due to the fact that the present invention is in particular directed to methods relating to the balloon of a balloon catheter that is in non-expanded state, the following comments shall generally be understood as referring to a non-expanded, that is deflated, state of the balloon, unless otherwise expressly mentioned. Moreover, the terms "diameter of the balloon catheter", "diameter of the balloon" as well as "outer diameter of the balloon catheter" and "outer diameter of the balloon" are used synonymously in the description below and shall always be understood as referring to the balloon portion of the catheter in the deflated state, unless explicitly noted otherwise. Likewise, for the purposes of this application the terms "balloon catheter" and "catheter" are used synonymously to refer to a catheter provided with a balloon, unless specific reference is made to a catheter that is not provided with a balloon.

The key parameters which have to be considered in the selection of a balloon catheter suitable for a given intervention include the length of the balloon and its nominal outer diameter when expanded. These two balloon parameters are, as a rule, adopted to suit the relevant characteristics of the stenosis. Among other factors, also the internal diameter and morphology of the affected vessel have to be taken into account when selecting a suitable balloon catheter. For example, the more convoluted a vessel is, the more flexible the balloon catheter must be that has been selected for this purpose. With respect to flexibility, the outer diameter of the balloon in non-expanded state is, among other things, also of significance. Since the balloon even in the unexpanded state, defines, as a rule, the area of the balloon catheter with the largest outer diameter, this constitutes another limiting factor in the selection of a suitable catheter. It must also be borne in mind that it will not be sufficient to simply advance the balloon catheter, even in its non-expanded state, through the vascular system to the target site where the lesion exists, but that it must as well be possible to place it correctly in position at the point of the lesion.

Therefore, several factors must be observed that influence the selection of an appropriate balloon catheter, among others the pliability of the catheter and particularly the pliability in the area of the balloon.

Basically, for an intervention aimed at widening a vessel, a balloon catheter is to be given preference that has the smallest possible outer diameter. Initially, a catheter should be as flexible as possible to enable it to be pushed through tortuous and/or narrow vessels on its way to the target vessel. In addition to the materials used, an essential factor for the flexibility of a balloon catheter is the outer diameter in the area of the balloon. It can thus be said in simplified terms that the smaller the outer diameter of a catheter, also in the area of the balloon, the easier it can be navigated or pushed forward also through tortuous and/or narrow vessel sections.

When selecting a catheter, it is therefore important to ensure its pliability resp. flexibility, also and particularly in the area of the folded balloon. In this context, flexibility has an influence on both the ease of catheter movement ("navigation") and the force required to advance the catheter "(pushability)". The more pliable, i.e. flexible, a balloon catheter is, the better and easier it can be pushed forward, even through tortuous vessel configurations.

As already mentioned above, before the balloon catheter can be expanded it must also be able to pass through the stenosis site to be treated. More specifically, the balloon of the catheter must be capable of being placed in the stenosis and then widen it as it expands. The more severe the stenosis, the more the vessel is occluded at this location, and consequently the smaller is the still open and thus passable area. It thus follows that such a stenosis can be passed easier or at all only with a balloon whose cross section is smaller than or equal to the passable area of the stenosis. Catheters having a smaller outer diameter are more likely to meet this requirement than those whose outer diameter is larger.

It is thus the goal to provide balloon catheters having the smallest possible outer diameter, so that they are suited and can be considered for a maximum number of interventions. Various techniques are known for reducing the outer diameter of a balloon in the non-expanded state.

Typically, the deflated balloon of a completed catheter is laid in folds. As required by the size of the balloon, different numbers of folds may be formed, which are subsequently wound up around the axis of the catheter in the same direction. With this arrangement, a first significant reduction of the outer diameter can already be achieved.

Viewing the cross-sectional representation of a balloon folded in this way, gaps can still be observed existing between the individual wound-up folds among themselves and between folds and the catheter shaft. With a view to reducing these gaps even more, various methods are proposed in the prior art. An example of this is the so-called cutback method, by means of which the folded balloon with the tube pulled over it is passed through a usually funnel-like nozzle. This causes the tube to be stretched resulting in a reduction of its diameter, which consequently also reduces the diameter of the balloon arranged within the tube. Such a method has been described in publication WO 2016/050303 A1.

However, reducing the balloon diameter via known methods always leads to a stiffening of the balloon as a result of its multilayer and folded arrangement. This arrangement causes reduced pliability in the area of the folded balloon, which can have a detrimental effect on the maneuverability and advancement of the catheter, particularly in highly tortuous vessels. Applying these prior art methods will also result in high mechanical loads acting on the balloon in some cases.

SUMMARY OF THE INVENTION

It is thus the objective of the present invention to provide a method that enables the outer diameter of a non-expanded balloon of a balloon catheter to be reduced without suffering the disadvantages of known methods.

This objective is achieved by an invention encompassing the characteristics of claim 1, with advantageous embodiments in each case being the subject of the dependent claims. It is to be noted that any features and characteristics individually included in the claims may also be combined with each other in an optional and technologically sensible manner so that they reveal further implementations or methods of the invention.

Within the meaning of the invention, the term "restriction element" shall be understood to refer to both band- or cord-like elongated objects which are particularly suitable for spirally wrapping around an elongated balloon, and ring elements which are suitable for sliding onto an elongated balloon.

For the sake of simplicity, the term "bands" will be used hereinafter for band- or cord-like restriction elements, and the term "rings" will be used to generally denote ring-shaped restriction elements.

As claimed by the present invention a method comprises at least the following steps:
(A) Provision of a balloon catheter;
(B) Attaching at least one restriction element to at least a portion of the balloon of the balloon catheter;
(C) Passing the balloon prepared in accordance with step (B) through an opening; and
(D) Applying a sheath to the balloon.

The balloon of the balloon catheter is preferably laid in folds before the restriction element is applied, but in principle the method can also be implemented with a non-folded balloon. Nevertheless, an initial diameter reduction by folding is to be considered useful since the diameter reduction to be achieved through the inventive method then only needs to be augmented and the folding moreover allows an orderly dilatation of the balloon.

As proposed by the invention, the attachment of the at least one restriction element to at least a portion of the balloon can be accomplished in a number of different ways.

When bands are used as restriction elements, attachment on the balloon is provided, for example, by means of a number of spiral or screwlike or helical wraps—which for simplicity reasons will be summarized and referred to in the following as spiral wraps or wrappings.

In the event rings are employed as restriction elements, their arrangement on the balloon is provided, for example, by sliding the rings onto the balloon. As a rule, several rings are placed onto the balloon, typically between 2 and 10, for example between 3 and 6.

A combination of rings and bands is conceivable.

Where spiral wraps are provided, such a wrapping shall preferably consist of only a single band. With a view to imprinting an appropriate spiral structure on the balloon, the spiral wraps are preferably arranged extending in one direction only. After passing through the opening this spiral structure remains even after the band or bands have been removed. A single-layer spiral wrap of the balloon is normally sufficient, also conceivable, however, is to apply a multi-layer wrapping comprising several bands.

The wrapping can be applied in such a way that there is still a small gap between each turn of the band, but the wrapping can also be arranged without any gaps existing. The wrapping of the balloon takes place preferably in such a way that a gap or gaps are provided, so that the windings or turns are spaced a certain distance from each other. Advantageously, these gaps are spaced apart between 0.5 and 7 mm, more preferably between 1 and 5 mm. The wrapping of the balloon with the band or bands should be as tight as possible, either by the wrapping itself being tight already, that is by exerting a tensile force acting in the longitudinal direction on the respective band, or by the respective band being pulled tight after wrapping, which in particular can be accomplished by exerting tensile forces to act on the ends.

In case bands are employed, flat bands having a certain width of ≥2 mm are preferred. Particularly preferred is a width ranging between 0.5 and 2 cm. In this context, width denotes the extension of the band parallel to the surface of the balloon and orthogonal to the longitudinal direction of the band. The length of the band shall be determined by the length and diameter of the balloon to be prepared and also depends on the type of winding and is to be selected as required.

When rings are used as restriction elements, the attachment of a plurality of rings is preferred. The individual rings can be arranged without any connection existing between them or strung together in a band, for example by providing suitable entanglements or interlacing, also in the form of knots.

The spacings described for spiral wraps also apply to the attachment of rings and, likewise, the dimensions described for bands can also be applied to rings.

Predetermined breaking points can be provided on the rings to simplify their removal. Similarly, the rings may be provided with withdrawal elements, particularly tab-like appendages that enable the rings to be easily grasped. Withdrawal elements of this nature may even be of help in the process of placing the rings in position.

A balloon that has been provided with restriction elements shall hereinafter be referred to as a "prepared balloon".

In an alternative embodiment, a sleeve can be placed around the prepared balloon in a further step (B1), that is a step following step (B) and taking place prior to step (C), with the length of the sleeve preferably corresponding at least to the length of the balloon. The inner diameter of the sleeve should preferably be selected such that the sleeve's inner wall has frictional contact with the balloon. A sleeve is understood to be a tubular or hose-shaped element.

The sleeve is provided to safeguard the sensitive balloon against damage as it is pulled through the opening and also serves to stabilize the position of the restriction elements, that is to prevent said elements from slipping or shifting during further processing. The additional provision of such a sleeve, preferably a tubular sleeve, is of particular advantage in the event rings are used as restriction elements.

Suitable materials to be used for the sleeve in particular comprise materials that cause low friction to ensure the material of the expandable element underneath is left undamaged. Polytetrafluoroethylene (PTFE, Teflon) is particularly suitable but other materials, especially plastic materials, which have low friction characteristics may also be put use.

The opening through which the prepared balloon is to be passed shall be configured such that, when the prepared balloon is passed through, the outer diameter of the balloon and, if applicable, of the sleeve are reduced, meaning, the inner diameter of the opening is preferably sized so as to be smaller than the outer diameter of the prepared balloon; on the other hand, however, it is not so much smaller as to make it virtually impossible for the prepared balloon to pass through. The same applies to a prepared balloon provided with a sleeve.

The diameter of the opening should usually be selected such that it is only possible to push the prepared balloon through the opening by exerting an appropriate amount of force, which then causes the reduction in diameter as desired.

As a rule, the opening has a circular cross section. Basically and within the meaning of the invention, opening denotes any kind of cutout or recess through which the prepared balloon can be passed. This may, for example, be a through-opening within an object or plate, but it may as well be a ring. Also considered as an opening within the scope of the invention is an opening that has a certain depth like a nozzle.

Advantageously, the opening has a tapered configuration, with a larger first inner diameter at the first end where the prepared balloon is introduced into the opening, and with a smaller second inner diameter at the second end through which the prepared balloon passes out of the opening.

The first inner diameter should be selected to enable an easy insertion of the prepared balloon fitted, if applicable, with a sleeve. The second inner diameter must be of such a size that drawing the prepared balloon, if applicable provided with sleeve, through the opening in actual fact results in a reduction in diameter; more precisely, the first inner diameter of the opening is equal to or larger than the outer diameter of the prepared balloon and the second inner diameter of the opening is smaller than the outer diameter of the prepared balloon.

Normally, when the prepared balloon has been passed through the opening and before applying the sheath, the restriction elements and, if applicable, the sleeve are removed from the balloon (step C1). The spiral or ring-shaped corrugation structure is imprinted on the balloon, respectively on the folds existing on the balloon by means of the restriction elements and the narrow opening, i.e. said structure is retained even when the restriction elements and, if applicable, the sleeve are removed. The imprinting of the structure described increases at the same time the balloon's flexibility, which is of advantage when navigating through blood vessels of narrow lumen.

However, it is also conceivable to leave the restriction elements and, if provided, the sleeve on the balloon and places the sheath over said elements. In this case, not only the sheath but in addition the restriction elements and, if provided, the sleeve must then be removed before the balloon catheter is put to use.

The sheath placed over the balloon serves as a protector of the balloon and safeguards it against damage etc. during storage. Moreover, if balloons are employed that are coated with active agents, the sheath ensures that said substances remain on the balloon and do not detach prematurely. Typically, the sheath used is of tubular configuration.

If thought expedient or necessary, step (C) during which the balloon diameter is reduced can be repeated until the desired diameter reduction is reached. Openings having a still smaller diameter can be used in each case so that when step (C) is repeated, the inner diameter of the opening is reduced each time as required.

Instead of or in addition to repeating step (C), steps (B), (C), and (C1) each may also be repeated, that is, not only the process of passing the balloon through an opening or passing it through a sequence of openings can be repeated, but also attaching and removing the restriction elements. Carrying out said steps as described above enables, for example, a tighter wrap to be applied or rings of smaller inner diameter to be used with a view to reducing the outer diameter of the balloon even more.

Similarly, it is as well possible in this context to repeat step (B1), i.e. providing the prepared balloon with a sleeve, for which purpose it is of course mandatory to first remove the old sleeve before a new one can be applied.

The balloon catheter proposed by the invention typically comprises lumens, preferably at least two lumens, with one lumen serving for the supply of fluid and pressurization and being connected to the interior of the balloon, while the other lumen serves to accommodate a guidewire that is initially pushed forward to the target site, with a view to subsequently moving the balloon catheter to the target site via the guidewire. In this context, essentially two different systems are known from prior art, namely over-the-wire (OTW) and rapid exchange (Rx) balloon catheters. The balloon catheter according to the invention can be either an OTW or an Rx balloon catheter. While in an OTW catheter the lumen for the guidewire extends from proximal to distal along the entire length of the catheter, an Rx catheter is designed to have a separate guidewire access port (Rx port) where the guidewire exits the catheter significantly distal to the proximal end of the catheter. Accordingly, in the case of an OTW balloon catheter, the lumens for fluid delivery and guidewire extend concentric or parallel to each other from the proximal end of the catheter up to the balloon, whereas in the case of an Rx catheter, this is only the case between the Rx port and the balloon. On the other hand, the section between the Rx port and the proximal end only has one lumen for fluid delivery. Typically, in areas where the catheter has been provided with two lumens, the lumens extend parallel to each other such that an inner lumen may also extend through the adequately sized outer lumen.

While step (C) is being carried out, which involves reducing the balloon diameter by passing the prepared balloon through an opening, the guidewire preferably extends through the lumen of the balloon catheter intended for this purpose. This prevents the lumen through which the guidewire extends from being compressed and narrowed. Regarding the subsequent application as a balloon catheter, it is essential in relation to the balloon catheter that the guidewire can be easily moved longitudinally in distal or proximal direction through the respective lumen, which is why narrowing of said lumen is disadvantageous. This is true regardless of whether the catheter is of OTW or Rx design, because when carrying out step (C) a radially inward force is exerted primarily in the balloon zone of the balloon catheter, since this zone has a considerably larger cross section than areas of the catheter where no balloon has been provided. However, both the OTW and Rx catheters have a guidewire lumen in the area of the balloon, the narrowing of which should be avoided.

Already during step (B) and, if applicable, (B1), the guidewire preferably extends through the guidewire lumen of the balloon. Narrowing of the guidewire lumen is avoided in this manner even when the restriction elements are tightly applied and tightened.

The selected material of the restriction elements should ensure that it does not adhere to any portion of the catheter. This requirement of a non-adherent restriction element is met in particular by materials containing polytetrafluoroethylene (PTFE).

In the event a multilayer attachment is provided, it is sufficient as a rule if the restriction elements that are directly resting on the balloon have non-adhesive properties, that is, are made, for instance, of materials containing PTFE.

The present invention has particular significance for drug-eluting balloons (DEB) which as a rule are of a cross section that is larger than that of non-loaded balloons, due to the fact that, for example, an active substance such as paclitaxel is deposited between the folds provided on the balloon in the contracted state. In such cases and in particular when very long balloons are to be handled this makes navigation/advancing within the blood vessel system difficult. Preferably, the active substances or agents are selected from the group: Tretinoin, orphan receptor agonists, elafin derivatives, corticosteroids, steroid hormones, paclitaxel, rapamycin, tacrolimus, hydrophobic proteins and/or substances modifying cell proliferation.

Aside from the method proposed by the invention, the invention also relates to a balloon catheter that is obtained according to the inventive method.

Basically, balloon catheters are sufficiently known from prior art and comprise an elongated catheter shaft extending from proximal to distal as well as a balloon which is arranged distally. With respect to its dimensions such a catheter is suitably designed for insertion into a body lumen, especially into a (blood) vessel system. The relevant dimensions of such catheters may vary depending on whether the blood vessel, for example, is a coronary artery, an intracranial blood vessel or an artery in the lower leg. Moreover, the balloon catheter is provided with means for delivering a fluid to the balloon, which may be a delivery/supply lumen extending over the length of the balloon catheter.

Furthermore, the inventive balloon catheter may not only serve for the elimination of stenoses and the local administration of active substances but additionally for the placement of a stent (endoprosthesis) in a body lumen. Stents are tubular supporting structures implanted into a body lumen, for example a blood vessel, with a view to keeping it permanently open. Stents of this nature may be of self-expanding design or expanded with the help of a balloon. For this purpose, the stent is crimped onto the balloon and introduced into the body lumen with the aid of a balloon catheter. At the desired placement site, the balloon is inflated by feeding in a fluid, which also causes the stent to expand and thus be anchored in the body lumen. Finally, the balloon is deflated and removed from the body lumen whereas the stent remains in place in the lumen.

At the proximal end of the balloon catheter, a so-called catheter hub is usually arranged, i.e. a connector for the device serving for fluid delivery and pressurization. The connector, for example, can be a conventional luer or luer-lock connection. Proximal is understood to mean toward the outside of the body, i.e., toward the attending physician, while distal shall be understood to denote the opposite direction, i.e., toward the blood vessel being treated. The balloon catheter is usually inserted into the human body in the groin area via the femoral artery.

Over the length of the balloon catheter radiopaque markers may be arranged at various positions, said markers serving the purpose of making the catheter visible on radiographs. In particular, said markers may be manufactured of platinum or a platinum alloy.

In comparison to the state of the art, the method proposed by the invention offers the advantage that the mechanical stresses acting on the balloon, and possibly causing damage to it, are reduced to a minimum. This is primarily due to the fact that the inventive restriction elements are directly arranged on the balloon by wrapping or sliding them on. In contrast to other methods, significantly lower tensile forces need be exerted in this case than in known prior art methods.

All statements made with respect to the manufacturing process shall apply accordingly to the balloon as well as the balloon catheter and vice versa.

Further elucidation of the invention is provided by way of examples through the enclosed figures. It should be noted that the figures show preferred embodiment variants of the invention, but the invention itself shall not be limited thereto. To the extent it is technically expedient, the invention comprises, in particular, any optional combinations of the technical features that are stated in the claims or in the description as being relevant to the invention.

BRIEF DESCRIPTION OF THE SEVERAL VIEWS OF THE DRAWINGS

Elucidation of the invention is provided by the following figures where

FIG. 1 shows a balloon of a balloon catheter provided with band-shaped restriction elements;

FIG. 2 is an illustration of the balloon according to FIG. 1 after tightening of the band-shaped restriction elements;

FIG. 3 shows the balloon according to FIG. 2 having been passed through an opening;

FIG. 4 shows a balloon of a balloon catheter provided with ring-shaped restriction elements;

FIG. 5 illustrates the balloon according to FIG. 4 after tightening of the ring-shaped restriction elements, and FIG. 6 shows the balloon according to FIG. 5 having been passed through an opening.

DESCRIPTION OF SPECIFIC EMBODIMENTS OF THE INVENTION

FIG. 1 shows a part of a balloon catheter, namely the catheter shaft 2 with the balloon 1 arranged at the distal end. A band 3, preferably made of PTFE material, is placed around the balloon 1 as a restriction element, resulting in a plurality of turns/windings 4.

FIG. 2 shows the balloon 1 from FIG. 1, but after the band-shaped restriction element 3 and the turns/windings 4 placed around the balloon 1 have been tightened. This already will cause the outer diameter of the balloon 1 to be significantly reduced, which, however, is still not sufficient.

FIG. 3 shows the result after passing the balloon 1 with a band-shaped restriction element 3 placed in turns/windings 4 through an opening not shown here. It can be seen that the outer diameter of the balloon 1 was reduced considerably. Subsequently, the band-shaped restriction element 3 can be removed and the balloon 1 be provided with a sheath as a protector.

FIG. 4 shows a part of a balloon catheter, namely the catheter shaft 2 with the balloon 1 arranged at the distal end. A plurality of ring-shaped restriction elements 3, preferably made of PTFE material, is placed around the balloon 1.

In FIG. 5 the balloon 1 from FIG. 4 is illustrated, however after the ring-shaped restriction elements 3 placed around the balloon 1 have contracted and as a result widened slightly. This already will cause the outer diameter of the balloon 1 to be significantly reduced, which, however, is still not sufficient.

FIG. 6 shows the result after passing the balloon 1 with the ring-shaped restriction elements 3 through an opening not shown here. It can be seen that the outer diameter of the balloon 1 was reduced considerably. Subsequently, the ring-shaped restriction element 3 can be removed and the balloon 1 be provided with a sheath as a protector.

The invention claimed is:

1. A method for reducing an outer diameter of a balloon of a balloon catheter in a non-expanded state, comprising the following steps:

(A) providing a balloon catheter;

(B) attaching at least one band-like element and/or at least one two ring elements to at least a portion of a balloon of the balloon catheter, thereby forming a prepared balloon, wherein:
  an arrangement of the at least one band-like element is carried out spirally, screw-like, or helically; and/or
  an arrangement of the at least two ring elements is carried out in the form of rings;
(C) passing the balloon prepared in accordance with step (B) through an opening to further reduce the outer diameter; and
(D) applying a sheath to the balloon.

2. The method according to claim 1, wherein step (C) is repeated until a desired outer diameter of the balloon is achieved.

3. The method according to claim 1, wherein the at least one band-like and/or at least one ring element is removed from the balloon in an additional step (C1), namely after step (C) and before step (D).

4. The method according to claim 3, wherein the steps (B) to (C1) are repeated until a desired outer diameter of the balloon (1) is achieved.

5. The method according to claim 1, wherein the balloon is provided with folds before applying the at least one band-like and/or at least one ring element pursuant to step (B).

6. The method according to claim 1, wherein in a step (B1) a sleeve, a length of which amounts to at least a length of the balloon, is slid over the prepared balloon, said step (B1) being carried out after step (B) but before step (C).

7. The method according to claim 1, wherein the balloon catheter is provided with a lumen for a guidewire extending at least through the balloon, wherein at least during step (C), the lumen contains a guidewire.

8. The method according to claim 1, wherein the at least one band-like and/or at least one ring element is made wholly or in part of polytetrafluoroethylene.

9. The method according to claim 1, wherein the at least one band-like and/or at least one ring element has a width of ≥2 mm.

10. The method according to claim 9, wherein the at least one band-like and/or at least one ring element has a width ranging between 0.5 and 2 cm.

11. The method according to claim 1 wherein a distance between individual windings of the band or the individual rings ranges between 0.5 and 7 mm.

12. The method according to claim 11, wherein the distance between the individual windings of the band or the individual rings ranges between 1 and 5 mm.

13. The method according to claim 1, wherein the opening has a tapered configuration, with a larger first inner diameter at a first end where the prepared balloon is introduced into the opening, and with a smaller second inner diameter at a second end through which the prepared balloon exits the opening.

* * * * *